United States Patent [19]

Labeyrie et al.

[11] 4,364,946

[45] Dec. 21, 1982

[54] METHOD OF TREATING INSUFFICIENCIES IN HEMATOSIS WITH ALMITRINE

[75] Inventors: Etienne Labeyrie; Jean-Pierre Poirier, both of Paris; Francoise Arnaud, La Garenne Colombes, all of France

[73] Assignee: Science Union et Cie, Suresnes, France

[21] Appl. No.: 294,014

[22] Filed: Aug. 18, 1981

[30] Foreign Application Priority Data

Aug. 18, 1980 [FR] France ................................ 80 18074

[51] Int. Cl.$^3$ ............................................ A61K 31/53
[52] U.S. Cl. .................................................... 424/249
[58] Field of Search .......................................... 424/249

[56] References Cited

U.S. PATENT DOCUMENTS 3,647,794  3/1972  Regnier et al. ..................... 424/249

FOREIGN PATENT DOCUMENTS 2019646  7/1973  France .

OTHER PUBLICATIONS

Vidal Dictionary, (1980) pp. 1295–1296.

Primary Examiner—Stanley J. Friedman
Attorney, Agent, or Firm—Gordon W. Hueschen

[57] ABSTRACT

A method of treating insufficiencies in hematosis, such as hypoxemia, cardiac insufficiency, and polyglobulia, involving treatment of a patient suffering from such insufficiency with the compound almitrine or a pharmaceutically-acceptable salt thereof in extremely low daily dosages, between 0.5 and 3 mg/kg orally or 0.05 to 0.3 mg/kg intravenously, an oral unit dosage form of the said active ingredient, containing between 20 and 70 mg of active ingredient together with a pharmaceutically-acceptable carrier or diluent, preferably about 50 mg of the active ingredient.

7 Claims, No Drawings

METHOD OF TREATING INSUFFICIENCIES IN HEMATOSIS WITH ALMITRINE

BACKGROUND OF THE INVENTION

1. Field of Invention

Methods of treating insufficiencies in hematosis such as hypoxemia, cardiac insufficiency, polyglobulia, and pharmaceutical compositions particularly adapted for use in such method.

2. Prior Art

The compound almitrine, as well as its pharmaceutically-acceptable acid addition salts, are known compounds which have been disclosed in French Pat. No. 2,019,646 and corresponding U.S. Pat. No. 3,647,794. These compounds have been disclosed as respiratory analeptics for treatment of respiratory insufficiencies in relatively high doses, representatively 1 to 5 mg/kg/day orally and 0.1 to 3.0 mg/kg/day intravenously in animals. The compound almitrine is also known as "DCI" and has the chemical name bis-4,6-(allylamino)-2{[bis-(4fluoro-phenyl)methyl]-4-piperazinyl}-triazine. Of particular interest according to the present invention is its bismethane sulfonate, as well as other pharmaceutically-acceptable acid addition salts thereof.

According to the "Vidal Dictionary" (a 1980 edition), pages 1295 and 1296, the compound almitrine is described under the brand name "Vectarion", a pharmaceutical specially named for almitrine, and recommends 1 to 3 mg/kg/day by perfusion for respiratory resuscitation or 0.5 to 1 mg/kg/day by slow direct intravenous drip for anesthesiology.

In such doses, almitrine increases ventilation and respiratory rate and decreases the amount of carbon dioxide in the arterial blood, the mechanism of action then taking place on peripheral receptors of the respiratory system as indicated in the foregoing cited patents. It has also been indicated there that, in such doses, almitrine has a vascular effect which enables it to maintain the blood flow despite hyperventilation. Further, in accord with the Vidal Dictionary, almitrine corrects disturbances in partial oxygen pressure and partial carbon dioxide pressure as well as in the pH. Finally, almitrine, in these doses, enables the correction of respiratory insufficiency, and therefore constitutes a respiratory analeptic which is used essentially for shock treatment inasmuch as, at the said high dosages, a muscular fatigue presents a serious side effect for a patient treated therewith. This muscular fatigue appears to result from the fact that almitrine acts upon chemical receptors in the aortic and carotid glomeruli through bulbo-protuberantial respiratory zones on muscles producing the respiratory movements, and previous employment of almitrine has been limited by the seriousness of such side effects.

THE ACTIVE INGREDIENT

The active ingredient of the compositions and method of the present invention is almitrine, which is bis-4,6-(allylamino)-2-{-[bis-(Afluoro-phenyl)-methyl]-4-piperazinyl}-triazine, having the formula shown on FIG. 1 or a pharmaceutically-acceptable salt thereof, such as an acid addition salt, especially the bismethane sulfonate salt thereof.

It has now surprisingly been found that almitrine, or a pharmaceutically-acceptable salt thereof, can be employed in some what lower doses than previously envisioned to provide an effective treatment of insufficiencies in hematosis, particularly those due to regulation of the local pulmonary perfusion, especially upon administration orally or intravenously, and particularly by the oral route.

OBJECTS OF THE INVENTION

It is an object of the present invention to provide a novel method for the treatment of insufficiencies in hematosis, such as hypoxemia, cardiac insufficiency, and polyglobulia which employs unprecedentedly low daily dosages and unit dosages of almitrine or a pharmaceutically-acceptable salt thereof.

SUMMARY OF THE INVENTION

The invention may be representatively summarized as follows:

An oral pharmaceutical composition in unit dosage form, useful in the treatment of insufficiencies in hematosis including hypoxemia, cardiac insufficiency, and polyglobulia, comprising as essential active ingredient the compound almitrine or a pharmaceutically-acceptable salt thereof, in an amount between about 20 and 70 mg, together with a pharmaceutically-acceptable oral pharmaceutical diluent; such composition wherein the amount of active ingredient is about 50 mg; such composition wherein the pharmaceutically-acceptable diluent is a solid pharmaceutical tableting adjuvant; such composition wherein the active ingredient is almitrine bismethane sulfonate.

Also, a method of treating insufficiencies in hematosis in thee patient suffering from such insufficiency comprising the step of administering to the said patient the compund almitrine or a pharmaceutically-acceptable salt thereof in an amount effective for such purpose by the oral or intravenous route, the said amount administered being 0.5 to 3 mg/kg/day by the oral route or 0.5 to 0.3 mg/kg/day by the intravenous route; such method wherein the administration is by the oral route; such method wherein the administration is by the intravenous route; such method wherein the administration of almitrine or a pharmaceutically-acceptable salt thereof is by the oral route;

such method wherein the insufficiency is a cardiac insufficiency; such method wherein the insufficiency is polyglobulia; such method wherein the compound administered is almitrine bismethane sulfonate; such method wherein the insufficiency in hematosis treated is hypoxemia.

A primary discovery according to the present invention is that almitrine, administered orally or intravenously, but preferably orally, in much smaller doses than previously employed as a respiratory analeptic, does not produce any substantial effect upon respiration but does prevent hematosis insufficiencies, such as cardiac failure, and reduces polyglobulia. An essential finding according to the present invention is, therefore, that the product almitrine, and the pharmaceutically-acceptable salts thereof, are useful in the prevention of blood disorders and cardiac failures.

From a current test, it appears that cardiac failure often occurs in patients having an excessively large X-ray heart image or other clinical sign of cardiac insufficiency, and that this failure can occur spontaneously or after excessive effort which results in severe physiological difficulties, mainly at the level of the encephalic structures and the liver. On the other hand, polyglobulia, or excess of red blood cells, is an aggravating factor of cardiac insufficiency, known to increase blood viscosity and consequently the load upon the heart. This polyglobulia is under the control of a renal harmone, namely, erythropoietine. In the past, patients suffering from polyglobulia were bled, and this was the only alternative. Treatment according to the present invention obviously offers a much more appropriate alternative. Actuation of the blood flow at the level of the alveolar structures results in more efficient ventilation/perfusion ratios and/or intake without modification of the respiratory rhythm and tidal volume, but in contrast with the results upon the employment of the previous much larger dosages of almitrine, as a respiratory analeptic, in which case the respiratory rhythm was accentuated, as well as the tidal flow, so as to increase the availability of oxygen to the pulmonary alveolas. Under such increased dosage regimens, however, the respiratory work of bronchitic patients was increased, and was inefficient at the alveolae level, and moreover, such dosages also induced an increase of oxygen consumption, all of which sometimes and frequently surpassed the benefits induced by the hyperventilation. Moreover, such dose has frequently produced undesirable side effects such as vomiting, coughing, and convulsions. Employment of the product almitrine as a respiratory analeptic avoided many of these problems in that it acted through the chemoreceptors of the aortic and carotidian glomus through the bulbo-protuberantial brain-stem respiratory areas, onto the muscles which create the respiratory movements, namely, mainly the diaphragm and accessorily squalens, the intercostal muscles, ceratus magnus, the abdominal wall, and the lombar musculatory mass. Thus, the effect of almitrine in high dosages did not produce the unwanted side effects of previous respiratory analeptics and its active dosages were much lower than its toxic dosages, giving it a desirable theraputic ratio. Nonetheless, as an analeptic, it was found to cause muscular tiredness or exhaustion which could be overwhelming for patients having a current propensity toward exhaustion, so that the previous main use of this product was in injectable preparations containing 1–3 mg/kg IV for use in respiratory revivification emergencies in intensive care units.

The present invention, although employing the same drug almitrine, approaches the problem of increasing the oxygen uptake by the blood in an entirely different and most unobvious way, as will now be described in more detail.

It has long been known that alveolar air flow being considered as constant, the rate of oxygen uptake from the alveolas into the blood depends upon repartition of blood flow inside of the lung. Otherwise stated, the alveolas receiving more or less the same quantity of air, the base of the lung receives much more blood than the top, by application of the law of gravity, resulting in a situation in which the alveolas at the top of the lung have considerably more air and relatively little blood so that the air will be poorly absorbed, whereas the alveolas at the base of the lung will have relatively little air and a large quantity of blood, which as a consequence will be minimally oxygenated. In the middle areas of the lung, where the ratio is approximately half air and half blood, the ideal condition allows an optimal transfer of air from the alveola to the blood. This phenomema is well known as the "regulation of optimal ventilation/perfusion ratios", and is described in most university student reference books, and can be readily assessed by isotopic techniques. It occurs via a local autonomous mechanism, the exact nature of which is not yet precisely known, but which is independent of the centrally-controlled respiratory-muscle work-activity as by means of an analeptic.

According to the present invention, it has now been found that almitrine, at a lower dose, at which it has no analeptic activity, has an unobvious and specific activity on the local regulation of the above-mentioned perfusion in lung alveolas. Accordingly, the present invention is at least partially based upon the discovery that the compound almitrine at such low doses induces great variations in the repartition of lung blood perfusion rates, leading to an optimization of the lung ventilation/perfusion ratio, without modifying the spirometric parameters of respiration, this property being particularly valuable and useful in the treatment of hypoxemias, especially chronic hypoxemias.

PREPARATION OF ALMITRINE AND ITS SALTS

Almitrine and its pharmaceutically-acceptable acid addition salts, particularly the bismethane sulfonate, but also the hydrochloric, hydrobromic, sulfuric, phosphoric, acetic, propionic, malic, fumaric, tartaric, citric, oxalic, benzoic, and other salts of organic and inorganic acids, are known and may be prepared as set forth in U.S. Pat. No. 3,647,794 or its French counterpart French Pat. No. 2,019,646 Still other additional pharmaceutically-acceptable salts may be employed if desired, and innumerable such salts will readily present themselves and be obvious to one skilled in the art.

When employing the active principle of the method of the invention in the form of an acid addition salt, the acid is selected so as to contain an anion which is non-toxic and pharmacologically acceptable, at least in usual therapeutic doses. Representative salts which may be included in this group are the hydrochlorides, hydrobromides, sulfates, acetates, phosphates, nitrates, quinates, tartrates, and maleates. Other acid addition salts are suitable and may be employed if desired. For example, fumaric, benzoic, ascorbic, pamoic, succinic, salicylic, bismethylenesalicylic, propionic, gluconic, malic, malonic, mandelic, cinnamic, citraconic, stearate, palmitic, itaconic, glycolic, benzenesulfonic, and sulfamic acids may also be employed as acid addition salt-forming acids. Organic and inorganic acids are suitable.

Salts with cation exchange resins may also be used, as they provide oral sustained release preparations since the free base or a biologically-absorbent moiety is released from these resin salts slowly and over an extended period of time. These resin salts, therefore, likewise fall within the scope of those utilizable as active principles according to the present invention. Still other pharmaceutically-acceptable salts may be employed if desired, and innumerable such salts will readily present themselves and be obvious to one skilled in the art.

In general, the active principle of the present invention can be conveniently prepared and isolated in conventional manner either in the form of the free base or an acid addition salt thereof. Indication of typical suitable acid addition salts has already been given in the foregoing. While it is preferred to isolate and employ the active principle of the present invention in the form of a solid or crystalline acid addition salt, if for any reason it is desired to employ the active ingredient in the form of the free base, it may be obtained according to conventional procedure, for example, by conducting the reaction for its production in a solvent and thereafter evaporating the solvent to obtain the reaction product as an almost colorless oil, or by dissolving an isolated hydrochloride or other salt in water, neutralizing with a base such as ammonia, ammonium hydroxide, sodium carbonate or other suitable alkaline material, extracting the liberated base with a suitable solvent such as ether or benzene, drying the extract, and evaporating to dryness in vacuo or fractionally distilling. Addition salts may also be made from the free base according to conventional procedure by taking up or dissolving the free base in a suitable solvent and acidifying with the selected acid, the salt of which is desired, which in many cases results in precipitation of the acid addition salt. In other cases the desired salt may be isolated by cooling the solution or by evaporating excess solvent, or in similar known manner for the isolation of acid addition salts. Certain of the acid addition salts may also be isolated directly from the reaction by adding the selected acid to a neutralized solvent solution of the reaction product. Dosage Forms Unit dosage forms for use according to the present invention may be of any suitable and/or conventional type. For oral administration, the unit dosage form generally contains about 20 to 70 mg of active ingredient, whether free base or salt, selected, preferably about 50 mg thereof. For intravenous administration in sterile solution, the unit dose usually contains 0.5 to 10 mg of the active ingredient selected, preferably about 5 mg thereof. As already stated, the selected compound is preferably administered together or in conjunction with a pharmaceutically-acceptable carrier.

According to the usual practice of the art, the active compound is therefore generally associated with a nontoxic pharmaceutical diluent or carrier which may be either a solid material or a liquid. Blend carriers are preferred for some applications. The compositions can take the form of tablets, powders, capsules, liquid solutions, emulsions or suspensions, or other dosage forms which are particularly useful for oral administration. Liquid or semi-liquid diluents may be employed for oral use. Such a medium can be or contain a solvent such as water. The only basic limitations of the liquid diluent used are compatibility and palatability. The compositions can take the form of almitrine or an acid addition salt thereof admixed with solid diluents and/or tableting adjuvants such as rice starch, corn starch, potato starch, lactose, sacharose, gelatin, talc, stearic acid, magnesium stearate, carboxymethylcellulose, gums such as gum acacia or tragacanth, chicle, agar agar, or the like. Any of the tableting materials used in pharmaceutical practive can be employed where there is no incompatability with the active ingredient or ingredients. The active ingredient can be tableted or otherwise compounded with or without other coactive materials. Alternatively, the active ingredient with or without active adjuvant material can be placed in the usual capsule of absorbable material, such as the usual gelatin capsule, and administered in this form. High concentrations of active ingredient can be employed by utilizing tablet triturates. In yet another embodiment, the powered active ingredient with adjuvant material can be placed into powder packets. Other examples of compositions in which the active ingredient may be embodied are as follows: the composition can be combined with foods of various kinds; it can be prepared in the form of a laminated or enteric coated tablet for prolonged action; it can be combined with an antacid or analgesic, e.g., aluminum hydroxide gel, calcium carbonate, magnesium oxide or trisilicate, acetylsalicylic acid, phenacetin, propoxyphen, or the like; it can be combined with phenobarbital or other sedative barbiturate or narcotic, for example, codeine or the like; it can be combined with local anesthetics effective in the gastrointestinal tract, such as procaine hydrochloride, novocaine, benzocaine, or the like; it can be combined with a diuretic compound, such as chlorthiazide, hydrochlorthiazide, or the like; or it may be combined with any other adjuvant or bulk-producing material, such as methylcellulose or carboxymethylcellulose, or combinations of the foregoing can be provided. Where the active ingredient is combined with one or more other pharmaceutically-active materials; it is of course necessary that the materials be compatible and that the physiological effect of the active ingredient of the present invention not be adversely affected thereby. Besides the foregoing mentioned forms, the compositions of the invention may also take the form of candies, soft drinks, gums, lozenges, syrups, elixirs, and the like. Reference is made to U.S. Pat. Nos. 1,907,203, 2,196,768, and 2,433,244 for suitable tablet coatings for lamination or enteric coatings; U.S. Pat. No. 2,875,130 for other sustained release type formulations which may be employed; to Remington on Pharmacy for various pharmaceutical formulations and procedures which may be employed; and to the specifications and examples of U.S. Pat. Nos. 2,753,288 and 2,881,113 for additional pharmaceutical forms, carriers and types of formulations and combinations in which the active ingredient of this invention may be substituted for the active ingredient of the patents in question. Suppositories or other compositions for rectal administration may be of any suitable or conventional type, for example, having the active ingredient dispersed in an ointment, wax, or polyethylene glycol base, preferably one which melts at or about body temperature, or otherwise in accord with the skill of the art in that particular area of medicine and drug delivery.

The proportion of active ingredient in the compositions of the present invention can be varied. It is only necessary that the selected active ingredient constitute an effective amount, i.e., such that a suitable dosage will be obtained consistent with the dosage form employed. Obviously several unit dosage forms may be administered at about the same time. In terms of percentages, the active ingredient in suitable pharmacteutical compositions which may be employed according to the present invention ordinarily comprise about 0.1 to about 80 weight percent, preferably about 0.5 to about 60 percent, varying because of the form of the composition involved from very low in liquid preparations and bulky tablets, as in combination with antacids or other coactive materials, to quite high in the case of tablets containing a single active appetite-suppressant compound or other solid-dosage forms. With most solid-dosage forms, the percentage is preferably about 10 to 60 percent by weight of the composition. In the preparation of unit dosgae forms, the skill of the art is entirely adequate to provide innumerable unit dosage forms and such will present themselves and will be apparent to anyone skilled in the art upon reading of this disclosure.

For intravenous injection, suitable sterile solutions are employed according to the usual skill of the art, which are ordinarily finished by filtration through a membrane filter, aspects filling into an ampule, and treatment in an autoclave, for e.g., twenty minutes, to provide the finished sterile solution in ampule form for ready administration.

DAILY DOSAGES

The daily dosages of the compound almitrine or a pharmaceutically-acceptable salt thereof, for the purposes of the present invention, are as follows:

0.5 to 3 mg/kg/day by the oral route and 0.05 to 0.3 mg/kg/day by the intravenous route, preferably about 1 mg/kg/day by the oral route and 0,1 mg/kg/day by the intravenous route.

METHOD OF THE INVENTION

The treatment of insufficiencies in hematosis in a patient suffering from such insufficiency, which may representatively be a hypoxia, particularly hypoxemia, acute or chronic, or a cardiac insufficiency, or the condition polyglobulia which tends to cause cardiac insufficiency, comprising the step of administering to the patient suffering from such insufficiency the compound almitrine or a pharmaceutically-acceptable salt thereof in an amount effective for such purpose by the oral or intravenous route, the said amount administered being 0.5 to 3 mg/kg/day by the oral route or 0.05 to 0.3 mg/kg/day by the intravenous route.

It has thus been found that the compositions of the invention, in doses of about 1 mg/kg/24 hours orally or about 0.1 mg/kg/24 hours intravenously (dose of the active product), possess very interesting and very unexpected pharmacological properties; in particular they make it possible to treat disturbances in hematosis which produce hypoxemias.

Hypoxemias are found in patients who do not justify treatment on basis of a respiratory analeptic since these patients do not show variation of the spirometric parameters and have a normal amount of carbon dioxide in their blood while having:

either a low level of the partial oxygen pressure in the blood ($PaO_2$)

or a normal level of the $PaO_2$ but a large decrease thereof upon effort, with a relatively long period of recuperation.

For such patients, the administration of the above-mentioned doses of almitrine produces an increase on the part of the $PaO_2$ or a more rapid return to the physiological level when the disturbance only appears upon effort.

On the other hand, such doses of almitrine have no effect on the $PaCO_2$.

The new and unexpected activity of the said low doses of almitrine cannot be explained by the present knowledge of the biological pharmacology of respiratory analeptics. This activity must employ a different mechanism.

It has been shown recently that almitrine in the high doses contemplated in the aforementioned French and U.S. patents acts via the branchial chemoreceptors.

These chemoreceptors have their origin in an archaic reflux tract which derives from fish. In these primitive animals, the branchial chemoreceptors control the frequency of the movement of the gills transmitting the information concerning the $PaCO_2$ in the blood arriving at the branchia. They consist of a mass of cells of neuroectodermic origin whose electrical activities are proportional to the $PaCO_2$; they are at the origin of the vascular structures which are related phylogenetically to the branchial arches, that is to say the aortic arch, the right subclavian vein and the carotids.

This reflux path exists and functions still in mammals, and in particular in humans. It is now known that high doses of almitrine have a respiratory analeptic activity by acting on this tract.

On the other hand, it seems that the newly discovered properties of the low doses of almitrine contemplated in the present patent application come from an action at an entirely different level. The action takes place in lungs which are without ventilatory modulation, without any substantial interference of the branchial chemoreceptors. In the present case one can speak of an autonomous effect of the lungs.

The complete independence between the path of the branchial chemoreceptors and the path of the lungs is very definite since the latter path appeared only very late in the evolution of the species. Thus fish, which take oxygen through their gills, have no lungs. The autonomous regulation by the lungs of the ventilation/perfusion ratio $\overset{\circ}{V}_A/\overset{\circ}{Q}$ takes place via the intraparenchymatous receptors on the vascular smooth muscles of the lung and it appears that the said low doses of almitrine exert a modulating control effect on this path.

The applicant has explained above in good faith the scientific hypotheses which seem to it most capable of explaining the action of small doses of almitrine, but it in no way desires to be limited by said mechanism with respect to the scope of its patent.

DETAILED DESCRIPTION OF THE INVENTION

The following preparations and examples in the form of pharmacological and clinical trials are given by way of illustration only and are not to be construed as limiting.

Description

The 50 mg tablets are white, oval, film-coated tablets of dimensions approx. 10.5×6.5 mm.

| Complete formulae (bis mesylate = bis methylsulfonate) | |
|---|---|
| | mg per tablet 50 mg tablets |
| Active constituent | |
| Almitrine bis mesylate | 50.0 |
| =almitrine base | 35.65 |
| Excipients | |
| Maize starch | 32.0 |
| Povidone | 9.0 |
| Lactose (direct compression) | 50.5 |
| Pregelatinised starch | 19.0 |
| Talc | 3.0 |
| Magnesium stearate | 1.5 |
| For a tablet core of | 165.0 mg |
| Hypromellose | 3.65 |
| Glycerol | 0.22 |
| Polyoxyethylene glycol 6000 | 0.165 |
| Magnesium stearate | 0.22 |
| Sodium lauryl sulphate | 0.045 |
| Colouring compound | |
| Titanium dioxide | 0.7 |
| For a tablet of | 170.0 mg |

| Placebo tablets (for comparative testing purposes) | | |
|---|---|---|
| | mg per tablet | |
| | 50 mg tablets | 100 mg tablets |
| Pregelatinised starch | 19.0 | 38.0 |
| Lactose | 137.0 | 274.0 |
| Povidone | 4.5 | 9.0 |

-continued

| Placebo tablets (for comparative testing purposes) | mg per tablet | |
|---|---|---|
| | 50 mg tablets | 100 mg tablets |
| Talc | 3.0 | 6.0 |
| Magnesium stearate | 1.5 | 3.0 |
| For a tablet core of | 165.0 mg | 330.0 mg |
| Hypromellose | 3.65 | 7.3 |
| Glycerol | 0.22 | 0.44 |
| Polyoxyethylene glycol 6000 | 0.165 | 0.33 |
| Magnesium stearate | 0.22 | 0.44 |
| Sodium lauryl sulphate | 0.045 | 0.09 |
| Titanium dioxide | 0.7 | 1.4 |
| For a tablet of | 170.0 mg | 340.0 mg |

CLINICAL EVALUATION

Clinical Trial I

The compound almitrine was tested in the form of a pharmaceutically-acceptable acid addition salt thereof, namely, the bismethane sulfonate, to determine the action of low dosages of the compound on heart failure risk.

A double blind study was accordingly carried out with two homogeneous groups of hospitalized patients suffering from compensated cardiac insufficiency.

In Group A, 31 patients were given one white oval tablet of the test compound containing 50 mg of almitrine according to the present invention.

In Group B, 37 patients were treated with a placebo, according to the description given herein for such placebo.

The treatment extended over a period of four (4) weeks, with each patient being given one tablet per day.

The results were as follows:

In Group A, only one heart failure could be identified, for a rate of 3 percent.

In Group B, six heart failures were identified, for a rate of 16 percent.

The conclusion from these studies is that the composition of the invention containing the extremely low dosage of almitrine had a protective effect upon the patients in Group A.

Clinical Trial II

This clinical evaluation was designed to test the action of the compound almitrine in extremely low dosages upon polyglobulia.

The test involved a double blind study with 24 subjects in two homogeneous groups of 12 each. The mean value of red blood cell count of the patients was 5.12 million per milliliter in each of the groups prior to treatment.

The tests were conducted over a period of one (1) month employing the composition of the present invention, namely, preceding almitrine tablets containing 50 mg of almitrine in the form of its bismethane sulfonate. The red blood cell count of the subjects involved, all of which had a red blood cell count in excess of 4.7 million per milliliter, was carried out over the course of an entire month and the results were taken at the end of the month.

In Group A, the subjects were treated with the aforesaid almitrine composition. They were given one (1) tablet daily by the oral route.

In Group B, each subject was treated with one (1) placebo tablet daily, according to the identification of the placebo tablet given elsewhere herein.

The results were as follows:

The resulting mean value for Group A was found to be 4.68 million per milliliter, which is normal, at the end of the one-month test period.

The resulting mean value for Group B was 5.18 million per milliliter, which figure had changed little from the starting point.

This test accordingly proves that the almitrine composition and method according to the present invention brings back to normal the number of red blood cells and thereby lowers the risk of cardiac failure through polyglobulia.

The composition and method of the invention can accordingly by recommended for the treatment of patients suffering from global cardiac insufficiency, whatever the symptoms, and for the treatment of patients having an elevated red blood cell count, so long as this is not of tumorous origin.

The composition according to the invention can accordingly contain 20–70 mg of almitrine, either as the free base or as a pharmaceutically-acceptable acid addition salt thereof, preferably about 50 mg of alimitrine, and a daily dose can comprise ½ to 5 tablets of 50 mg each, more broadly stated, the oral dosage recommended being 0.5 to 3 mg/kg/day and the intravenous recommended dosage being 0.05 to 0.3 mg/kg/day.

It is to be understood that the invention is not to be limited to the exact details of operation or exact compounds, compositions, methods, or procedures shown and described, as obvious modifications and equivalents will be apparent to one skilled in the art.

We claim:

1. A method of treating insufficiencies in hematosis in a patient suffering from such insufficiency comprising the step of administering to the said patient the compound almitrine or a pharmaceutically-acceptable salt thereof in an amount effective for such purpose by the oral or intravenous route, the said amount administered being 0.5 to 3 mg/kg/day by the oral route or 0.05 to 0.3 mg/kg/day by the intravenous route.

2. The method of claim 1, wherein the administration is by the oral route.

3. The method of claim 1, wherein the administration is by the intravenous route.

4. The method of claim 1, wherein the compound administered is almitrine bismethane sulfonate.

5. The method of claim 1, wherein the insufficiency in hematosis treated is hypoxemia.

6. The method of claim 1, wherein the insufficiency is polyglobulia.

7. The method of claim 1, wherein the insufficiency is a cardiac insufficiency.

* * * * *

UNITED STATES PATENT AND TRADEMARK OFFICE
CERTIFICATE OF CORRECTION

PATENT NO. : 4,364,946

DATED : December 21, 1982

INVENTOR(S) : Etienne Labeyrie, Jean-Pierre Poirier and Francoise Arnaud

It is certified that error appears in the above-identified patent and that said Letters Patent is hereby corrected as shown below:

Col. 1, line 61; "-(Afluoro-" should read -- -(4fluoro- --
Col. 1, lines 62 and 63; delete ", having the formula shown on FIG. 1"
Col. 2, line 33; "thee" should read -- the --
Col. 2, line 35; "compund" should read -- compound --
Col. 3, line 4; "harmone," should read -- hormone, --
Col. 3, line 38; "theraputic" should read -- therapeutic --
Col. 5, line 21; "Dosage Forms" is a heading and should be one line down and on that line by itself
Col. 5, lines 51 and 52; "practive" should read -- practice --
Col. 6, line 48; "pharmacteutical" should read -- pharmaceutical --
Col. 6, line 60; "dosgae" should read -- dosage --
Col. 6, line 67; "aspects" should read -- aseptic --
Col. 7, line 59; "reflux" should read -- reflex --
Col. 8, line 1; "reflux" should read -- reflex --
Col. 10, line 22; "by" should read -- be --

Signed and Sealed this

Fifth Day of November 1985

[SEAL]

Attest:

DONALD J. QUIGG

Attesting Officer

Commissioner of Patents and Trademarks